United States Patent [19]
Labrie et al.

[11] Patent Number: 5,393,785
[45] Date of Patent: Feb. 28, 1995

[54] THERAPEUTIC ANTIESTROGENS

[75] Inventors: Fernand Labrie; Yves Merand, both of Quebec, Canada

[73] Assignee: Endorecherche, Inc., Quebec, Canada

[21] Appl. No.: 913,746

[22] Filed: Jul. 14, 1992

Related U.S. Application Data

[63] Continuation of Ser. No. 265,150, Oct. 31, 1988, abandoned.

[51] Int. Cl.$^6$ ............... A61K 31/165; A61K 31/12
[52] U.S. Cl. ............... 514/622; 514/617; 514/680; 514/681; 514/510; 564/204
[58] Field of Search ............... 514/622, 510, 680, 681, 514/617; 564/204

[56] References Cited

U.S. PATENT DOCUMENTS

| | | | |
|---|---|---|---|
| 3,396,169 | 8/1968 | Lednicer et al. | 260/294.7 |
| 4,338,122 | 6/1982 | Wheeler | 514/681 |
| 4,358,461 | 11/1982 | Maki et al. | 514/681 |
| 4,382,094 | 5/1983 | Goudie et al. | 514/681 |
| 4,659,516 | 4/1987 | Bowler et al. | 260/397.5 |
| 4,732,912 | 3/1988 | Pilgrim et al. | 514/510 |
| 4,751,240 | 6/1988 | Bowler et al. | 514/510 |
| 4,904,661 | 2/1990 | Pilgrim et al. | 514/237.5 |
| 5,098,903 | 3/1992 | Magarian et al. | 514/255 |

FOREIGN PATENT DOCUMENTS

| | | |
|---|---|---|
| 0138504 | 2/1987 | European Pat. Off. . |
| 470310 | 8/1990 | European Pat. Off. . |
| 9010462 | 9/1990 | WIPO . |
| 9117749 | 5/1991 | WIPO . |
| 9221669 | 12/1992 | WIPO . |

OTHER PUBLICATIONS

Jones, et al., "Synthesis and Antiestrogenic Activity of (3,4–Dihydro–2–(4–Methyoxyphenly)–1–Naphthalenyl)(4–(2–(1–Pyrrolidinyl–Ethoxy)–Phenyl) Methanone, Meth Anesulfonic Acid Salt", *Journal of Medicinal Chemistry, vol. 22, No. 8 (1979).*

Wakeling and Bowler, *J. Steroid Biochem.*, 30:141–147, 1988.

*Primary Examiner*—Raymond J. Henley, III
*Assistant Examiner*—T. J. Criares
*Attorney, Agent, or Firm*—Ostrolenk, Faber, Gerb & Soffen

[57] ABSTRACT

Novel antiestrogenic compounds are disclosed for use in therapeutic preparations for treatment of estrogen-dependent diseases. The compounds are specified diphenylethane and diphenylethylene analogs which show strong affinity for estrogen receptors but substantially lack the capacity to activate such receptors or otherwise act as agonists.

4 Claims, 2 Drawing Sheets

○----○ ESTRADIOL,

□—□ DIETHYLSTILBESTROL

●—● ICI 164384 (WAKELING AE AND BOWLER J. 1987; J. ENDOCR. 112, R7-R10),

△--△ EM-142 (AN ANTIESTROGEN IN ACCORDANCE WITH THE INVENTION SYNTHESIZED IN EXAMPLE 1, HEREIN).

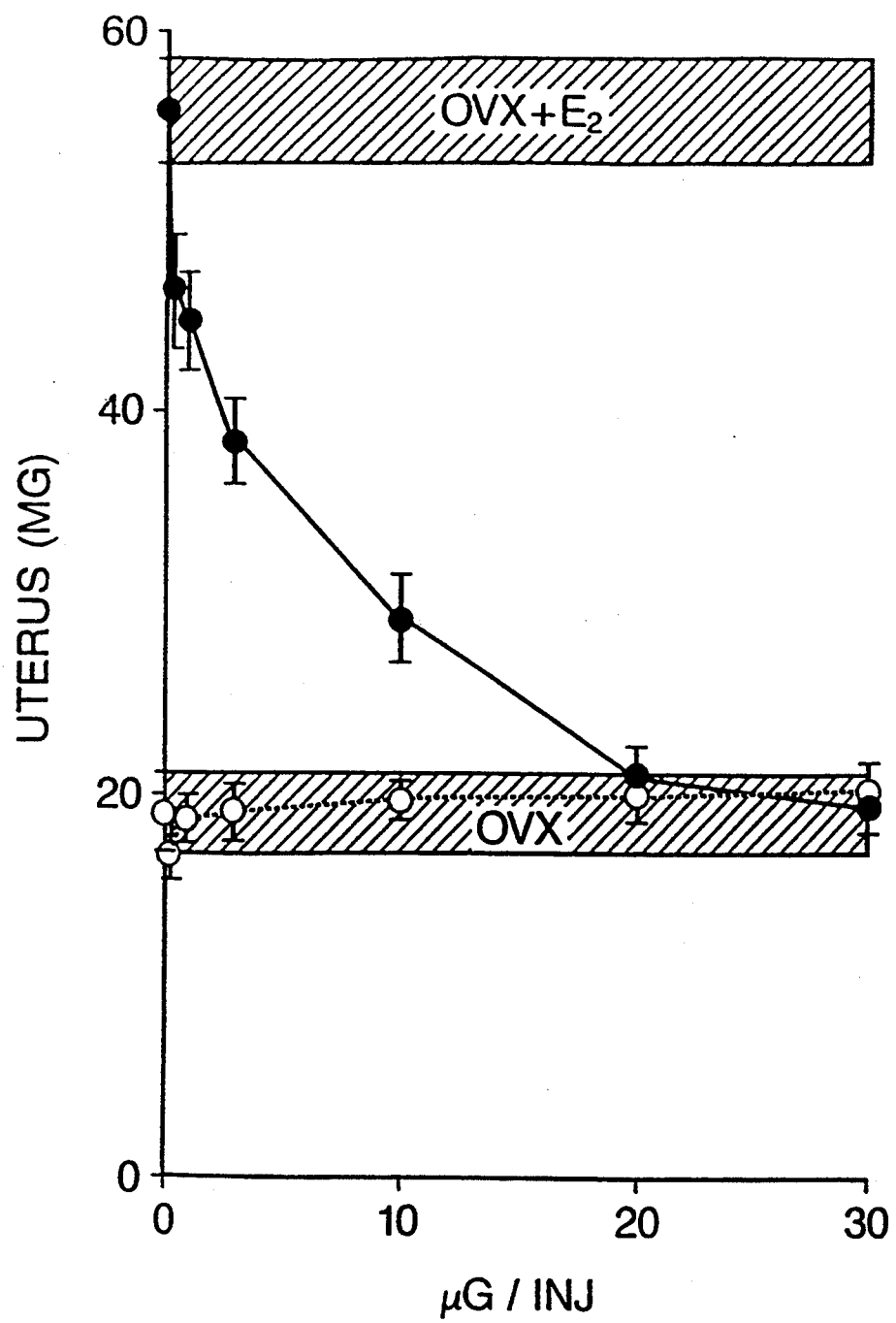

THERAPEUTIC ANTIESTROGENS

RELATED APPLICATION

This is a continuation of application Ser. No. 07/265,150, filed on Oct. 31, 1988, now abandoned.

BACKGROUND OF THE INVENTION

1. Field of the Invention

This invention relates to novel antiestrogen compounds having effective antagonistic capability while lacking agonistic effects. More particularly, certain preferred enbodiments of the invention relate to certain non steroidal diphenylethane or diphenylethylene analogs which have high affinity for estrogen receptors but do not activate such receptors.

2. Brief Description of the Prior Art

For the treatment of certain estrogen-dependent diseases, it is important to greatly reduce, or, if possible, eliminate estrogen-induced effects. Alternative or concurrent therapy to administration of antiestrogens could involve attempts to block the production of estrogens such that none is available to activate receptor sites. However, prior art methods for blocking estrogen production and/or reducing estrogen concentrations are not satisfactory and have only partial efficacy in inhibiting estrogen-induced functions. Moreover, it is possible that even in the total absence of estrogens, unoccupied estrogen receptors may be biologically active. See Simard and Labrie, "Keoxifene shows pure antiestrogenic activity in pituitary gonadotrophs": Mol. Cell. Endocrinol. 39: (1985) 141-144, especially page 144. Hence, antiestrogens may produce greater therapeutic results than therapy which only inhibits estrogen production.

Antiestrogens may have a significant therapeutic effect in slowing or stopping the progress of estrogen-dependent diseases, such as female breast cancer. Known antiestrogens have affinity for estrogen receptors and are at least moderately effective in blocking these receptors and preventing the formation of estrogen/receptor complex. Because this complex activates numerous estrogen-induced functions, blocking the formation of the complex substantially prevents or retards these estrogen-induced functions. However, prior art antiestrogens, while blocking the receptors, may themselves activate receptors, especially under in vivo conditions, and thus induce estrogenic effects. This "agonistic" activity of prior art antiestrogens can greatly diminish the therapeutic effectiveness of the antiestrogen.

There is, therefore, a need in the art for antiestrogens which effectively block estrogen receptors with minimal or no agonistic effect. Numerous compounds have been tried in the art with mixed results. Known antiestrogens continue to exhibit undesirable agonistic activity. See, for instance, Wakeling and Bowler, "Steroidal Pure Antioestrogens", J. Endocrinol. 112 (1987) R7-R10. The net effectiveness of prior art compounds is determined by the balance between their agonistic and antagonistic activities. Certain steroidal derivatives similar to those disclosed in the foregoing article, and which are stated to have antioestrogenic effect, are set forth in Bowler et al., U.S. Pat. No. 4, 659,516.

In U.S. Pat. No. 4,094,994, it is disclosed that the use of antiestrogens inhibit certain human breast tumor cells.

H. Mouridsen et al., Cancer Treatm. Rev. 5 (1978) 131-141, discloses that Tamoxifen, an antiestrogen, is effective in remission of advanced breast cancer in about 30 percent of the women patients treated.

The combined use of the antiestrogen Tamoxifen and a luteinizing hormone-releasing hormone agonist, Buserelin, is also known for treatment of breast cancer. See, for instance, Klijn et al. J. Steroid Biochem. 420 (no. 6B) (1984) 1381. The objective remission of such cancers, however, remains unacceptably low.

In U.S. Pat. No. 4,659,516, Bowler et al. report antiestrogenic activity for certain 7α substituted derivatives of estradiol.

OBJECTS OF THE INVENTION

It is an object of the present invention to provide non steroidal diphenylethane or diphenylethylene pure antiestrogens for therapeutic use.

It is another object to provide an antiestrogen having good affinity for estrogen receptors, but substantially lacking undesirable agonistic activity regarding these receptors.

It is another object of the invention to provide a therapeutic antiestrogenic composition useful in the treatment of estrogen-related diseases. These diseases include, but are not limited to breast cancer, uterine cancer, ovarian cancer, endometriosis, uterine fibroma, precocious puberty and benign prostatic hyperplasia.

SUMMARY OF THE INVENTION

The above and other objects are accomplished by providing a pharmaceutical composition comprising a therapeutically effective amount of diphenylethane or diphenylethylene derivatives specified herein. As used herein, the terms $R_1$, $R_2$ ... $R_{12}$ refer to substituents whose locations on the diphenylethyl framework is illustrated below:

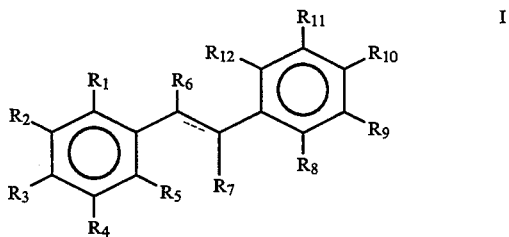

where the dotted line represents an optional double bond of Z or E configuration. Unless specifically designated to the contrary, the carbon bearing substituents may have either R or S stereochemistry. In some embodiments, the optional double bond is not present. When the optional double bond is not present, $R_6$ and $R_7$ may each represent two independent-selected substituents. In certain preferred embodiments, a salt of the specified compounds may be used. Molecular structures set forth herein may be substituted or unsubstituted at any position where substituents are not specifically defined. Those carbon atoms having substituents defined may optionally be further substituted by a second substituent. As used herein, the term "lower", when describing a carbon-containing moiety, means a moiety having 8 or fewer carbon atoms. For instance, a "lower alkyl" means a $C_1$ to $C_8$ alkyl.

Certain preferred substituents include, but are not limited to the following:

$R_1$, $R_5$, $R_8$, and $R_{12}$ are preferably independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitro, nitrile and nitroso.

$R_2$, $R_4$, $R_9$ and $R_{11}$ are preferably independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitrile, nitro, nitroso, azido, ($C_1$–$C_7$) alkanyol mercuryl, lower alkylamino, dilower alkylamino, $AXR_{21}$, $Y_7$—$A^1$[$Y$—$A^{11}$]$_u$—$XR_{21}$, and $A^1$—[$Y$—$A^{11}$]$_u$—$XR_{21}$ wherein:

A is straight- or branched-chain ($C_1$–$C_{30}$) alkylene, ($C_2$–$C_{30}$) alkenylene, ($C_2$–$C_{30}$) alkynylene, fluoro-substituted analogs of the foregoing, wherein u is an integer from 0 to 5, wherein $Y_7$ is absent or selected from the group consisting of carbonyl and carboxyl, $A^1$ and $A^{11}$ may be the same or different and are independently either absent or selected from the group consisting of straight- or branched-chain alkylene, straight- or branched-chain alkynylene, straight or branched-chain alkenylene, phenylene and fluoro-substituted analogs of the foregoing, wherein $A^1$ and $A^{11}$ together have a total of from 3 to 20 carbon atoms and Y is selected from the group consisting of —O—, —S—, —Se—, —SO—, —$SO_2$—, —CO—, —$NR_{22}$—, —$SiR_{22}R_{22}$—, —$CR_{22}OR_{22}$—, —$NR_{22}CO$—, —$NR_{22}CS$—, —$CONR_{22}$—, —COO—, —COS—, —SCO—, —CSS—, —SCS—, —OCO— and phenylene (wherein $R_{22}$ being hydrogen or lower alkyl), wherein $R_{21}$ is selected from the group consisting of hydrogen, straight or branched-chain lower alkyl, lower alkenyl or lower alkynyl, ($C_3$–$C_7$) cycloalkyl, halogeno(lower)alkyl, carboxy(lower)alkyl, (lower)alkoxycarbonyl(lower)alkyl, ($C_6$–$C_{10}$) aryl, ($C_6$–$C_{10}$)arylalkyl, di(lower)alkylamino(lower)alkyl and fluoro-substituted analogs of the foregoing, and wherein X is selected from the group consisting of —$CONR_{23}$—, —$CSNR_{23}$—, —$NR_{24}CO$—, —$NR_{24}CS$—, —$NR_{24}CONR_{23}$—, $$-NR_{24}-\overset{NR_{25}}{\overset{\|}{C}}-NR_{23},$$

—$SO_2NR_{23}$—, —CO—, —CSS—, —SCS—, —O—, —$NR_{23}$—, —(NO)$R_{23}$—, —(PO)$R_{23}$—, —$NR_{24}COO$—, —$NR_{24}SO_2$—, —S—, —SO— and —$SO_2$— (wherein $R_{23}$ being selected from the group consisting of hydrogen, lower alkyl, a species which, together with $R_{21}$, forms a saturated or unsaturated heterocyclic ring having at least one nitrogen atom and in certain embodiments, at least one other heteroatom selected from the group consisting of oxygen, sulfur, silicon, selenium and nitrogen, and fluoro-substituted analogs of the foregoing, and $R_{24}$ being hydrogen or lower alkyl, and $R_{25}$ being hydrogen, nitrile or nitro). In certain preferred embodiments, $XR_{21}$ forms a tetrazole ring.

$R_3$ and $R_{10}$ are preferably independently selected from the group consisting of hydrogen, hydroxyl, halogen, lower alkyl, lower alkoxy, lower alkoxy carbonyloxy, carboxyl, ($C_1$–$C_{20}$) alkanoyloxy, ($C_3$–$C_{20}$) alkenoyloxy, ($C_3$–$C_{20}$) alkynoyloxy, ($C_7$–$C_{11}$) aroyloxy and alkylsilyloxy.

$R_6$ and $R_7$ are preferably independently selected from the group consisting of hydrogen, amino, lower alkylamino, dilower alkyl amino, nitro, nitrile, nitroso, halogen, lower alkyl, lower alkenyl, lower alkynyl, halogeno lower alkyl, halogeno lower alkenyl, halogeno lower alkynyl, alkyl sulfonyl, aryl sulfonyl, a substituted 5 to 7 member heterocyclic ring having at least one heteroatom (selected from oxygen, sulfur, silicon, selenium, nitrogen), —$(CH_2)_sW$ (wherein W is nitrile hydroxyl, azido, nitroso, alkoxy, nitro, thionitrile, halogen, alkyl sulfonyl or aryl sulfonyl and s is an integer from 1 to 6), a moiety of the formula:

II wherein:

F is absent or selected from the group consisting of alkyl, carbonyl or carboxyl, wherein the phenyl ring may be halogenated, wherein $R_{61}$ is hydrogen, hydroxyl, halogen, lower alkyl, lower alkenyl, lower alkynyl, nitrile, nitro, nitroso or $X_6(CH_2)_nY_6$ ($X_6$ being selected from the group consisting of —O—, —S—, —Se—, —SO—, —$SO_2$— and —CO—, and $Y_6$ being selected from the group consisting of hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n being an integer from 1 to 6, preferably 3), $AXR_{21}$, $Y_7$—$A^1$—[$Y$—$A^{11}$]$_u$—$XR_{21}$, and $A^1$—[$Y$—$A^{11}$]$_u$—$XR_{21}$, wherein:

A is selected from the group consisting of straight- or branched-chain ($C_1$–$C_{30}$) alkylene, ($C_2$–$C_{30}$) alkenylene, ($C_2$–$C_{30}$)alkynylene and fluoro-substituted analogs of the foregoing, wherein u is an integer from 0 to 5, wherein $Y_7$ is absent or is selected from the group consisting of carbonyl, carboxyl, —$CH_2S$— and —$CH_2O$—, wherein $A^1$ and $A^{11}$ may be the same or different and may be absent or selected from the group consisting of straight- or branched-chain alkylene, straight- or branched-chain alkynylene, straight or branched chain alkenylene, phenylene and fluoro-substituted analogs of the foregoing, wherein $A^1$ and $A^{11}$ together have a total of from 2 to 30 carbon atoms, wherein Y is selected from the group consisting of —O—, —S—, —Se—, —SO—, —$SO_2$—, —CO—, —$NR_{22}$—, —$SiR_{22}R_{22}$—, —$CR_{22}OR_{22}$—; —$NR_{22}CO$—, —$NR_{22}CS$—, —$CONR_{22}$—, —$CSNR_{22}$—, —COO—, —COS—, —SCO—, —CSS—, —SCS—, —OCO— and phenylene ($R_{22}$ being hydrogen or lower alkyl), wherein $R_{21}$ is selected from the group consisting of hydrogen, straight or branched chain lower alkyl, lower alkenyl, lower alkynyl, ($C_3$–$C_7$) cycloalkyl, halogeno(lower) alkyl, carboxy(lower)alkyl, (lower)alkoxycarbonyl(lower)alkyl, ($C_6$–$C_{10}$)aryl, ($C_7$–$C_{11}$)arylalkyl, di(lower) alkylamino (lower) alkyl and fluoro-substituted analogs of the foregoing, wherein X is selected from the group consisting of —$CONR_{23}$—, —$CSNR_{23}$—, —$NR_{24}CO$—, —$NR_{24}CS$—, —$NR_{24}CONR_{23}$—, $$-NR_{24}-\overset{NR_{25}}{\overset{\|}{C}}-NR_{23}-,$$

—$SO_2NR_{23}$—, —CO—, —CSS—, —SCS—, —O—, —$NR_{23}$—, —(NO)$R_{23}$—, —(PO)$R_{23}$—, —$NR_{24}COO$—, —$NR_{24}SO_2$—, —S—, —SO— and —$SO_2$— ($R_{23}$ being selected from the group consisting of hydrogen, lower alkyl and a species which, together with $R_{21}$, forms a saturated or unsaturated heterocyclic ring having at least one nitrogen atom and, in certain embodiments at least one other heteroatom selected from the group consisting of oxygen, sulfur, silicon, selenium and nitrogen, and fluoro- substituted analogs of the foregoing, $R_{24}$ being hydrogen or lower alkyl and $R_{25}$ being hydrogen, nitrile or nitro). In certain preferred embodiments, $XR_{21}$ forms a tetrazole ring.

$R_6$ and $R_7$ may also be a species which, in combination with another substituent of general molecular formula I, forms a moiety selected from the group consisting of: —$CH_2$—, CHX, $CX_2$ (X being halogen, carboxyl or alkoxycarbonyl), —O—, —S—, —Se—, >N—CN, >$NR_{29}$ and >$NCO_2R_{29}$ ($R_{29}$ being hydrogen or lower alkyl), lower alkylene, —$(CH_2)_rO(CH_2)_s$—, —$(CH_2)_rS(CH_2)_s$—, —$(CH_2)_rSe(CH_2)_s$—, —$(CH_2)_rSO(CH_2)_s$—, —$(CH_2)_rSO_2(CH_2)_s$—, —$(CH_2)_rCO(CH_2)_s$—, —$(CH_2)_rNR_{22}(CH_2)_s$—, —$(CH_2)_rSiR_{22}R_{22}(CH_2)_s$— or —$(CH_2)_rCR_{22}OR_{22}(CH_2)_s$— (wherein $R_{22}$ being hydrogen or lower alkyl, r and s being independent integers from 0 to 3), a moiety of the formula:

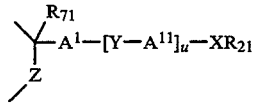

wherein:

$A^1$, Y, $A^{11}$, u, X and $R_{21}$ are as defined above, wherein Z is absent or is selected from the group consisting of lower alkylene, halogeno lower alkylene,—$(CH_2)_nO$—, —$(CH_2)_nS$—, —$(CH_2)_nSe$—, —$(CH_2)_nSO$—, —$(CH_2)_nSO_2$—, —$(CH_2)_nCO$—, —$(CH_2)_nNR_{22}$—, —$(CH_2)_nSiR_{22}R_{22}$— and —$(CH_2)_nCR_{22}OR_{22}$—, $R_{22}$ is as defined above, n being an integer from 0 to 3, and $R_{71}$ being selected from a group consisting of hydrogen, hydroxyl, halogen, lower alkyl, lower alkoxy and lower alkylsilyl, a moiety of the formula:

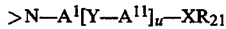

wherein N is nitrogen atom and $A^1$, Y, $A^{11}$, u, X and $R_{21}$ are as defined above.

In preferred embodiments, moieties which are combinations of R groups from general molecular structure I, are combinations of $R_6$ and $R_7$, $R_6$ with $R_1$ or $R_{12}$, or $R_7$ with $R_5$ or $R_8$.

BRIEF DESCRIPTION OF DRAWINGS

FIG. 2 illustrates the effect of the indicated doses of EM-142 injected twice daily (b.i.d.) on uterine weight (mg) in adult female ovariectomized Balb/C mice treated for 4.5 days in the presence or absence of simultaneous treatment with 17β-estradiot (0.01 μg, b.i.d.).

DETAILED DESCRIPTION OF CERTAIN PREFERRED EMBODIMENTS

Figure 1:
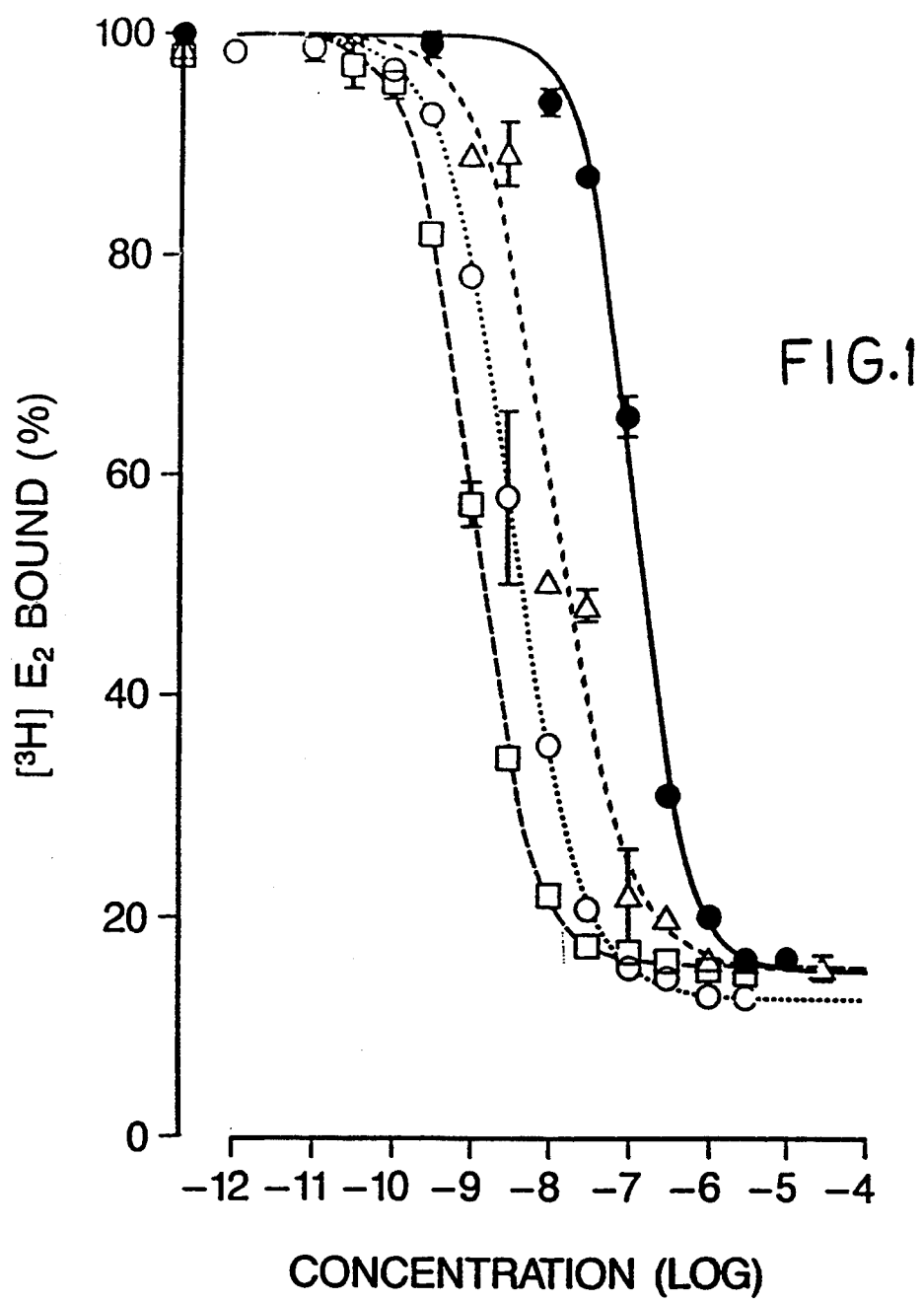
FIG. 1 illustrates a competition binding assay of the affinity of estradiol, diethylstilbestrol, ICI 164384 (Wakeling A. E. and Bowler J., 1987; J. Endocr. 112, R7-R10) and EM-142 (an antiestrogen in accordance with the invention synthesized in example 1, herein) for the rat uterine cytosol receptor (Asselin et al., 1978; J. Steroid Biochem. 9:1079-1082).

In certain preferred embodiments of the invention, the $R_3$ and $R_{10}$ substituents are hydroxyl, ($C_1$-$C_{20}$) alkanoyloxy, ($C_3$-$C_{20}$) alkenoyloxy, ($C_3$-$C_{20}$) alkynoyloxy, ($C_7$-$C_{10}$) aroyloxy and/or the $R_7$ substituent is $A^1$—[Y—$A^{11}$]u—X—$R_{21}$. It is also preferred that the $R_7$ substituent have between about 7 and 20 carbon atoms. It is preferred that $R_9$ be a hydrogen or $A^1$-[Y—$A^{11}$]u—X—$R_{21}$. It is also preferred that $R_6$ be lower alkyl, ethyl, fluoroethyl, or $(CH_2)_2W$, wherein W is a halogen or lower alkoxy. In certain embodiments, therapeutic compositions may comprise one or more compounds represented by Formula I. Preferably, at least one antiestrogenic compound is represented by the formula:

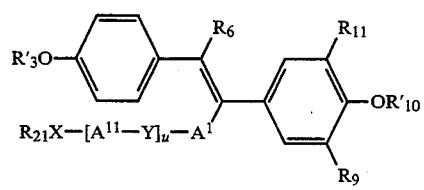

wherein $A^1$, $A^{11}$, Y, u, X and $R_{21}$ are defined as previously for $R_6$ and $R_7$ in the formula I, wherein the double bond is in trans configuration, wherein $R'_3$ and $R'_{10}$ are hydrogen alkyl ($C_1$-$C_{20}$) alkanoyl ($C_3$-$C_{20}$) alkenoyl, ($C_3$-$C_{20}$) alkynoyl or ($C_7$-$C_{11}$) aroyl, wherein $R_6$ is preferably selected from the group consisting of hydrogen, nitro, nitrile, halogen, lower alkyl, lower alkenyl, lower alkynyl halogeno lower alkyl, halogeno lower alkenyl, halogeno lower alkynyl, alkyl sulfonyl, aryl sulfonyl, a substituted 5 to 7 member heterocyclic ring having at least one hetero atom (selected from oxygen, sulfur, silicon, selenium, nitrogen), —$(CH_2)_sW$ (wherein W is nitrile, hydroxyl, azido, nitroso, alkoxy, nitro, thionitrile, halogen, alkyl sulfonyl, aryl sulfonyl and s is an integer from 1 to 6), or has the formula:

wherein:

F is absent or selected from the group consisting of alkyl, carbonyl or carboxyl, wherein the phenyl ring may be halogenated, wherein $R_{61}$ is hydrogen, hydroxyl, halogen, lower alkyl, lower alkenyl, lower alkynyl, nitrile, nitro, nitroso or $X_6(CH_2)_nY_6$, wherein $X_6$ is selected from the group consisting —O—, —S—, —Se—, —SO—, —$SO_2$— and —CO—, and $Y_6$ is selected from the group consisting hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n is an integer from 1 to 6 preferably 3.

$R_9$ and $R_{11}$ are preferably independently selected from the group consisting of hydrogen, hydroxyl, halogen, lower alkyl, lower alkoxy, lower alkylsilyl, amino, nitrile, nitro, nitroso, azido, lower alkylamino, dilower alkylamino $AXR_{21}$ and $A^1$—[Y—$A^{11}$]u—$XR_{21}$, wherein A, $A^1$, $A^{11}$, Y, X, $R_{21}$ and u are as defined previously for $R_6$ and $R_7$.

Pharmaceutical compositions comprising therapeutically effective amounts of one or more compounds represented by Formula I may be prepared wherein a pharmaceutically acceptable diluent or carrier is added. The diluent or carrier will vary in accordance with known techniques depending upon the manner in which the pharmaceutical composition is to be administered. A composition suitable for oral administration may preferably contain from about 1 mg to about 1500 mg of an antiestrogen in accordance with the invention. A composition suitable for parenteral administration preferably contains a carrier and an antiestrogen in accordance with the invention at a concentration sufficient to introduce from about 1 mg to about 1000 mg of the antiestrogen per 50 kg of body-weight per day. This concentration will, of course, vary with the volume flow at which the pharmaceutical composition is being administered.

In certain alternative embodiments, the pharmaceutical composition of the invention may be formulated for sustained release in accordance with known techniques. These sustained release formulations are preferably prepared in an appropriate manner for either oral, intramuscular, or subcutaneous administration.

Other alternative preferred embodiments include pharmaceutical compositions comprising therapeutically effective amounts of compounds of the formula:

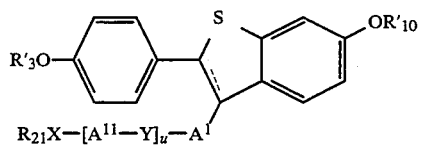

VI wherein the dotted line represents optional double bond, wherein $R'_3$, $R'_{10}$, $A^1$, Y, $A^{11}$, X, $R_{21}$ and u are defined as previously in formula V especially $A^1$—$[Y—A^{11}]_u$—$XR_{21}$ is —CO—p—$C_6H_4$—O—$(CH_2)_n$CONR$_{21}$R$_{22}$ wherein $R_{21}$ and $R_{22}$ are defined as previously for $R_6$ or $R_7$ in formula I and n is an integer of 1 to 15, or:

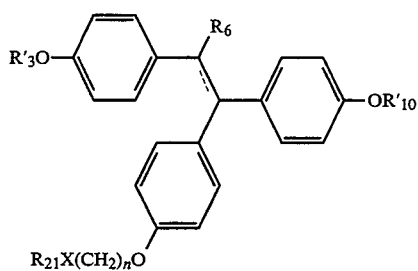

VII wherein the dotted line represents optional double bond, especially in trans configuration, wherein $R'_3$, $R'_{10}$, $R_6$ are defined as previously, wherein $R_{21}$ is selected from the group consisting of hydrogen, straight- or branched-chain lower alkyl, lower alkenyl or lower alkynyl, ($C_3$-$C_7$) cycloalkyl, halogeno(lower)alkyl, carboxy(lower)alkyl, (lower)alkoxycarbonyl(lower)alkyl, ($C_6$-$C_{10}$)aryl, ($C_7$-$C_{11}$)arylalkyl, di(lower)alkylamino(lower)alkyl and fluoro-substituted analogs of the foregoing, wherein X is —CONR$_{23}$—, —CSNR$_{23}$—, NR$_{24}$CO—, —NR$_{24}$CS—, —NR$_{24}$CONR$_{23}$—, $$—NR_{24}—\overset{\overset{NR_{25}}{\|}}{C}—NR_{23}—,$$

—SO$_2$NR$_{23}$—, —CO—, —CSS—, —SCS—, —O—, —NR$_{23}$—, —(NO)R$_{23}$—, —(PO)R$_{23}$—, —NR$_2$-4COO—, —NR$_{24}$SO$_2$—, —S—, —SO— or —SO$_2$ —, wherein $R_{23}$ is selected from the group consisting of hydrogen, lower alkyl and a species which, together with $R_{21}$, forms a saturated or unsaturated heterocyclic ring having at least one nitrogen atom and fluoro-substituted analogs of the foregoing, wherein $R_{24}$ is hydrogen or lower alkyl and wherein $R_{25}$ is hydrogen, nitrile or nitro; or $XR_{21}$ forms a tetrazole ring.

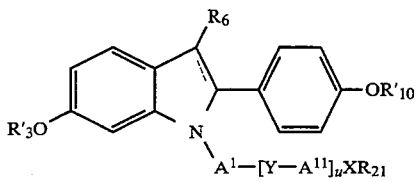

VIII wherein the dotted line represents optional double bond wherein $R'_3$, $R_6$, $R'_{10}$, $A^1$, $A^{11}$, Y, X, $R_{21}$ and u are as defined previously, or

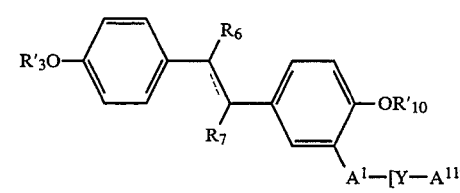

IX wherein the dotted line represents optional double bond especially in trans configuration, wherein $R'_3$, $R'_{10}$, $R_6$, $A^1$, $A^{11}$, Y, X, $R_{21}$ and u are defined as previously, wherein $R_7$ is preferably selected from the group consisting of hydrogen, halogen, lower alkyl, amino, nitro, nitroso, nitrile, lower alkylamino and dilower alkylamino, or

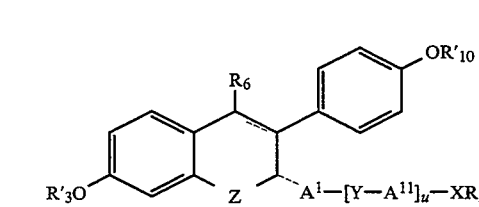

X wherein the dotted line represents optional double bond wherein $R'_3$, $R'_{10}$, $A^1$, $A^{11}$, Y, X, $R_{21}$ and u are defined as previously, wherein $A^1$—$[Y—A^{11}]_u XR_{21}$ is preferably in α configuration and wherein Z is absent or selected from the group consisting of lower alkylene, halogeno lower alkylene, —(CH$_2$)$_n$O—, —(CH$_2$)$_n$S—, —(CH$_2$)$_n$Se—, —(CH$_2$)$_n$SO—, —(CH$_2$)$_n$SO$_2$—, —(CH$_2$)$_n$CO—, —(CH$_2$)$_n$NR$_{22}$—, —(CH$_2$)$_n$SiR$_{22}$R$_{22}$— or —(CH$_2$)$_n$CR$_{22}$OR$_{22}$ (wherein $R_{22}$ is defined as previously and n is an integer from 0 to 3).

Set forth below is a detailed description of preferred synthetic techniques for producing certain preferred antiestrogens in accordance with the invention.

EXAMPLE 1 - Synthesis of Preferred Antiestrogens

Instrumentation

IR spectra were obtained in a Perkin-Elmer spectrometer 1310. UV spectra were recorded in methanol on a Beckman DU-6 spectrometer. H-NMR spectra were obtained at 200 MHz on a Varian XL-200 spectrometer. Chemical shifts are reported in ppm units with tetramethylsilane as internal standard. Mass spectra were obtained on Micromass 16F spectrometer.

N-butyl,N-methyl-12,13-Bis(4-hydroxyphenyl)-12-pentadecenoic amide (EM-142, compound 5 with x=10)

The synthesis of this compound is described in the scheme I were x=10.

12, 13 - Bis (4-methoxyphenyl)-11-pentadecenol (3)

4'-methoxy-2-ethyl,2-(4-methoxyphenyl) acetophenone (2) (710 mg, 2.5 mmol, prepared from desoxyanisoin, ethyl bromide and LDA by a known method) in THF (10 ml) are added, under argon, to Grignard reagent prepared from 11-bromo-tetrahydropyranyl undecanol (6.6 g, 19.7 mmoles) and magnesium (0.6 g, 24.7 mmoles) and THF (10 ml). The mixture was stirred for 18 hours, then acidified with 1N HCl and extracted three times with ether. The organic phase was washed with water (X3), dried over anhydrous magnesium sulfate, and evaporated under reduced pressure. The residue was chromatographed on Silica-gel (Kieselgel, 60F254, Merck, 0.063–0.200 mm, 100 g). Elution with a mixture of hexane - ethyl acetate (9:1 v/v) gave 12,13-Bis-(4-methoxyphenyl)-tetrahydropyranyl pentadecan-1,12-diol (991 mg, 76%) as a mixture of diastereoisomers; colorless oil, IR $\nu_{max}$ (neat) 3480, 1600 cm$^{-1}$; $^1$H-NMR ($\delta$,CDCl$_3$); 0.62 (3H, t, J=7.3 Hz, CH$_2$CH$_3$), 2.73 (1H, 2d, J=9.7 Hz, —CHCH$_2$CH$_3$), 3.25–4.00 (4H, m, —CH$_2$OCHOCH$_2$—), 3.76 and 3.79 (6H, 2s, —OCH$_3$), 4.57 (1H, t, J=1.1 Hz, —O$_2$—CH—CH$_2$) and 6.71 -7.30 (8H, m,H-Ar)ppm. MS m/e=523 (M+—H$_2$O).

The above diastereoisomers (920 mg, 1.8 mmol) dissolved in methanol (30 ml) and 5N HCl (5 ml) was refluxed for 1 hour, then collected, and extracted three times with ether. The organic layer was washed with water, dried over anhydrous magnesium sulfate, evaporated under reduced pressure to dryness and finally chromatographed on silica gel (Kiesegel, 60F254, 0.063-0.200 mm, Merck, 100 g). Elution with a mixture of hexane-ethyl acetate (7:3 v/v) gave 12,13- Bis(4-methoxyphenyl)-11-pentadecenol (3) (710 mg, 65% from compound 2), colorless oil, IR, $\nu_{max}$ (neat), 3340, 1600, 1030 cm$^{-1}$; UV $\lambda_{max}$ (log $\epsilon$)=231 (4.27) nm; $^1$H-NMR ($\delta$, CDCl$_3$), 0.88 (3H, t, J=7.3 Hz, —CH$_2$CH$_3$), 3.30 (1H, t, J=9.7 Hz, —CH—CH$_2$,CH$_3$), 3.63 (2 H, t, J=6.6 Hz, —CH$_2$OH), 3.76 and 3.78 (6H, 2s, —OCH$_3$), 5.51 (1H, t, J=8.8 Hz,1 —C=CH—) and 6.63-7.10 8H, m, H-Ar) ppm; MS m/e=438 (M+).

N-butyl, N-methyl, 12,13-Bis (4-methoxyphenyl) -11-pentadecenoic amide (4).

To a cooled solution of alcohol 3 (710 mg, 1.56 mmol) in acetone (17 ml) was added Jones' reagent (8N-chromic acid solution, 0.77 ml). After 30 minutes, isopropanol (5 ml) was added and the mixture was poured in water and extracted three times with ethyl acetate. The organic layer was washed twice with brine, dried over magnesium sulfate and evaporated to dryness. The crude 12,13-Bis (4-methoxyphenyl)-11-pantadecenoic acid was used in the next step without purification. To its solution in anhydrous methylene chloride (4 ml) at −10° C. was added, under stirring, triisobutylamine (470 μl, 1.96 mmol) and isobutylchloroformate (280 μl, 2.1 mmol). After 40 minutes, N-methylbutylamine (1.5 ml) was added and the mixture was stirred at room temperature during 1 hour. Methylene chloride (50 ml) was added. The organic solution was washed with 1N HCl, saturated sodium bicarbonate solution and water (3X), dried on magnesium sulfate and evaporated to dryness. The residue was purified by "Flash chromatography" on silica gel (Kieselgel 60, Merck, unter 0.063 mm, 50 g). Elution with a mixture of hexane-ethyl acetate (4:1 v/v) gave N-butyl, N-methyl-12,13-Bis (4-methoxyphenyl)-11-pentadecenoic amide (4), (549 mg, 68%) colorless oil; IR $\nu_{max}$(neat) 1640, 1600 cm$^{-1}$; UV $\lambda_{max}$(log $\epsilon$)=230 (4.39) nm; $^1$H-NMR ($\delta$, CDCl$_3$), 0.85–0.98 (6H, m, 2—CH$_2$CH$_3$), 2.27 (2H, t, J=7.1 Hz, CH$_2$CON), 2.91 and 2.96 (3H, 2s, —NCH$_3$), 3.25–3.36 (3H, m, —NCH$_2$— and CH$_3$CH$_2$ CH—), 3.77 and 3.78 (6H, 2s, OCH$_3$), 5.50 (1H, J=7.1 Hz, —C=CH—) and 6.69-7.01 (8H, m, H-Ar) ppm; MS m/e=521 (M+).

N-butyl, N-methyl-12,13-Bis(4-hydroxyphenyl)-12-pentadecenoic amide (EM-142, compound 5 with x=10)

To the above dimethoxy amide 4 (117 mg, 0.22 mmol) in CH$_2$Cl$_2$ (1 ml) at 0° C. was added, under argon, 1.0M borane tribromide (675 μl). The solution was stirred for 1 hour, then poured into water and extracted with ether (3x). The organic solution was washed with water, dried on magnesium sulfate, and evaporated to dryness. The residue was purified by "Flash chromatography" on silica gel (Kieselgel 60, Merck, unter 0.063 mm, 30 g). Elution with a mixture of hexane-ethyl acetate (4:1 v/v) gave N-butyl, N-methyl-12,13-Bis (4-hydroxyphenyl)-12-pentadecenoic amide (EM-142, compound 5 with x=10) (34 mg, 31%), colorless oil, IR $\nu_{max}$ (neat) 3300, 1600 cm$^{-1}$; UV $\lambda_{max}$ (log $\epsilon$)=235 (4.25) nm; $^1$H-NMR ($\delta$, CDCl$_3$), 0.76 (3H, t, J=7.3 Hz, —CH$_2$CH$_3$), 0.96 (3H, t, J=7.3 Hz, N (CH$_2$)$_3$CH$_3$), 2,05–2.20 (4H, m, CH$_2$—C=C—CH$_2$—), 2.35 (2H, t,J=7.0 Hz, —CH$_2$CON—), 2.97 and 3.00 (3H, s, —NCH$_3$), 3.29 and 3.41 (2H, 2t, J=7.3Hz, —N—CH$_2$—), and 6.59-7.09 (8H, m, H-Ar) ppm; MS m/e=493 (M+).

SCHEME I

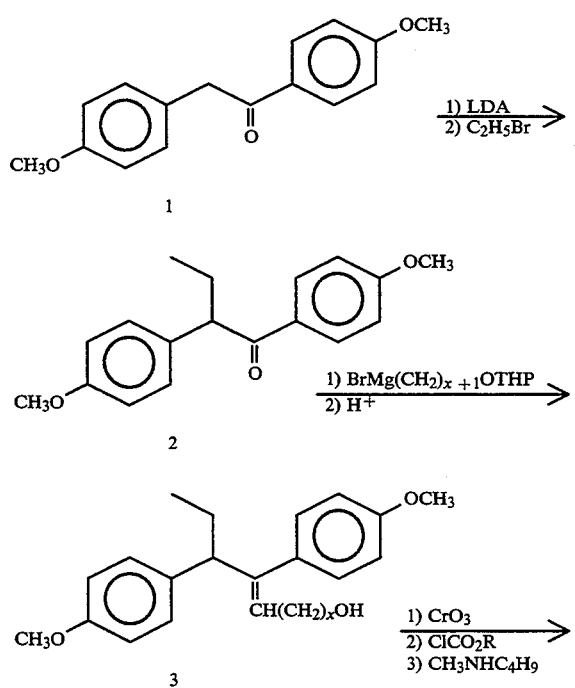

-continued
SCHEME I

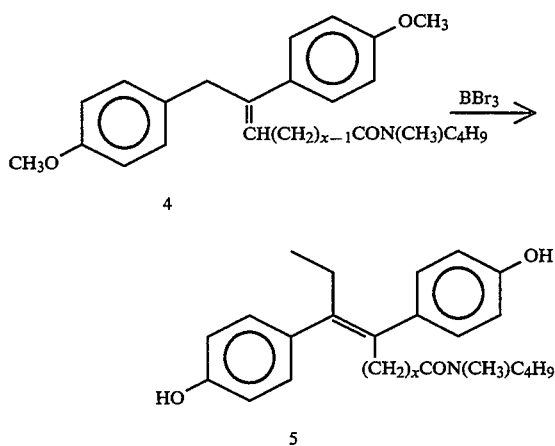

Example 2

Effectiveness of antiestrogen synthesized in Example 1

EM-142 from example 1 was tested by competition binding on the rat uterine cytosol estrogen receptor with [$^3$H]estradiol according to Asselin et al. (1976) procedure. FIG. 1 shows the binding affinity of EM-142 compared with estradiol, diethylstilbestrol and ICI 164384 (Wakeling and Bowler, 1987). (Incubation was performed at 25° C. for 3 hours). It can be seen that EM-142 is only 3 times less potent than 17β-estradiol itself while being more potent than the antiestrogen ICI 164384.

The antiestrogenic activity of EM-142 was measured in vivo by inhibition of the estradiol-induced stimulation of uterine weight in adult female ovariectomized Balb/c mice (body weight=19-20 g) sacrificed five days after ovariectomy. EM-142, and/or estradiol contained in ethanol were injected subcutaneously in the appropriate groups in a solution of 0.9% (w/v) sodium chloride and 1% (w/v) gelatin at different concentrations in 0.2 ml for EM-142, twice daily, starting on the day of ovariectomy for a total of 9 injections. Estradiol was injected at the dose of 0.01 μg in 0.2 ml, twice daily, starting on the morning after ovariectomy for a total of 8 injections.

After sacrifice, the uteri were rapidly removed, freed from fat and connective tissue and weighted. Results shown in FIG. 2 are the means ± SEM of groups of 9-10 mice. It can be seen that the very low dose of 0.3 μg already has a significant inhibitory effect of an $E_2$-induced uterine growth and that a complete reversal of $E_2$ effect is obtained at higher doses. A half-maximal inhibitory effect is in fact observed at approximately 3 μg while, at the doses used, 20 μg causes a complete reversal of estrogenic action. Note that EM-142 has no estrogenic effect on uterine weight, thus demonstrating its potent antiestrogenic activity.

Set forth below are some flow charts illustrating a number of preferred synthesis schemes for certain preferred antiestrogens in accordance with the invention. The steps set forth below are set forth merely by way of examples. Those of skill in the art will readily recognize alternative synthetic pathways and variations capable of producing a variety of antiestrogens in accordance with the invention.

Synthesis B
N-butyl, N-methyl-12, 13-Bis-(4-hydroxyphenyl) pentadecanoic amide (6)

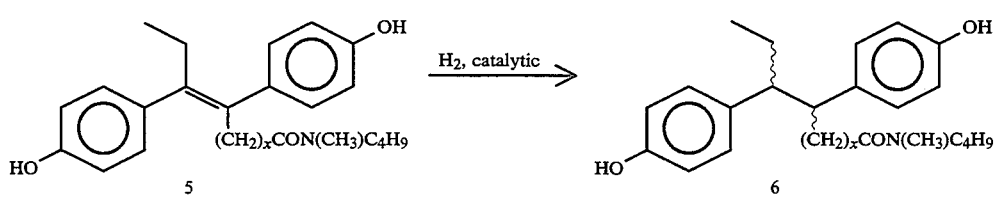

Synthisis C
N-butyl, N-methyl-5-[4-[(2-[4-hydroxyphenyl] benzothiophen-3-yl)formyl] phenoxyl] hexanioc amide (12)

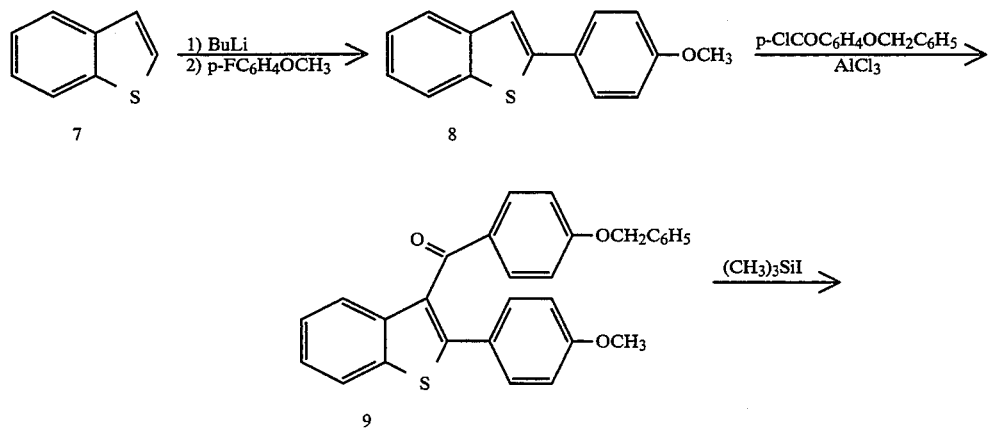

-continued
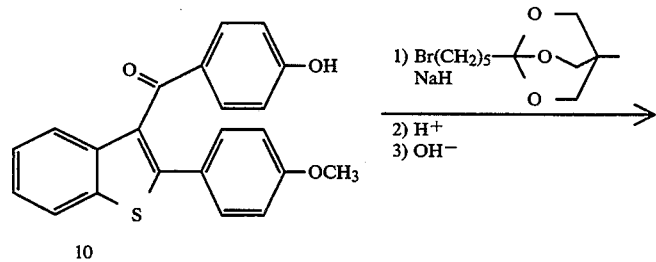
10
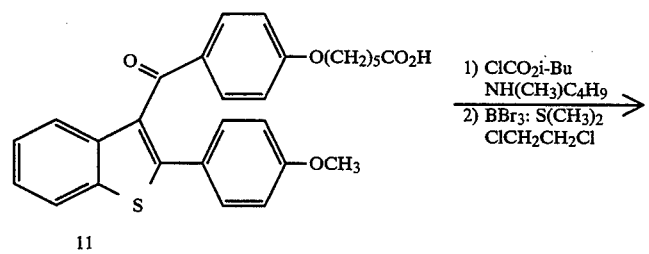
11
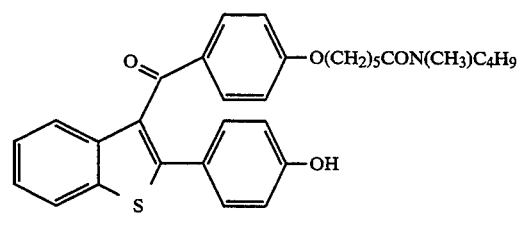
12
Synthesis D
N-butyl, N-methyl-6-[p-(trans-1', 2'-bis (4"-hydroxyphenyl)-1'-butenyl) phenoxyl] heptanoic amide (18)
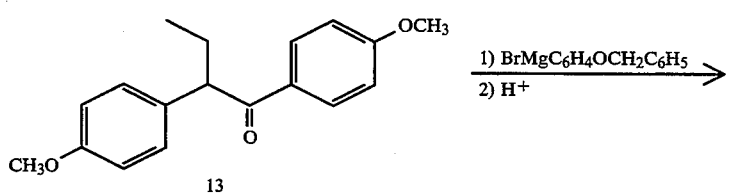
13
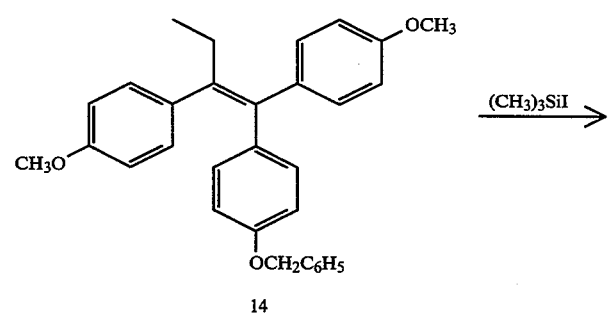
14
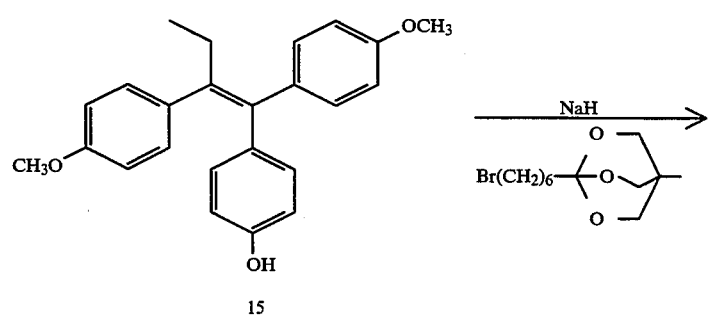
15

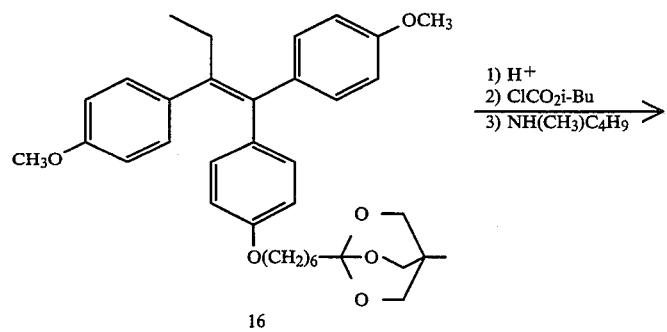
16
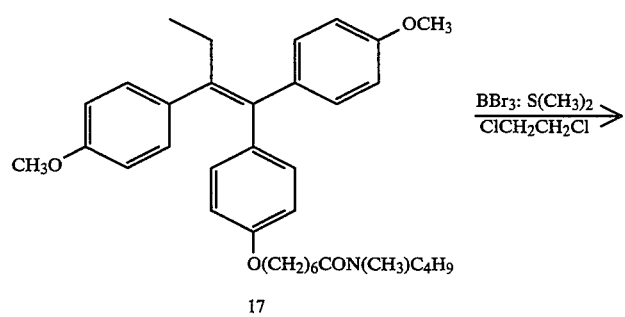
17
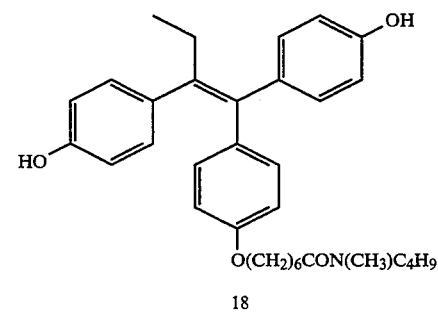
18
Synthesis E
N-butyl, N-methyl-(6'-hydroxy, 2'-(4''-hydroxyphenyl)-3'methyl indol-N'-yl) undecanoic amide (22)
The starting material (19) is synthesized by the Bischler indole synthesis as described previously (Von Angeres, E., Prekajac, J., Strohmeier, J., J. Med. Chem. 27: 1439 (1984)).
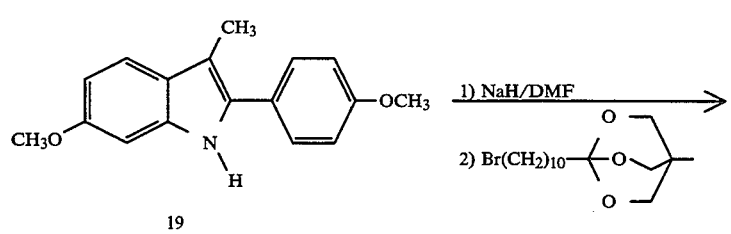
19
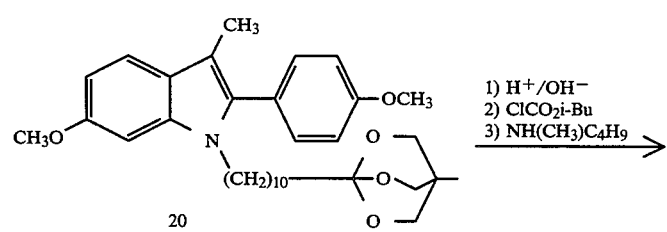
20

17 5,393,785 18
-continued
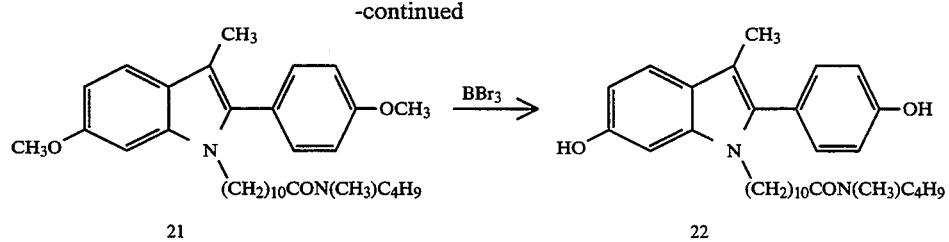
Synthesis F
N-butyl, N-methyl-[4, 4'-(1, 2-diethyl-1, 2-ethanydiyl) bis-phenol-3-yl) undecanoic amide (28)
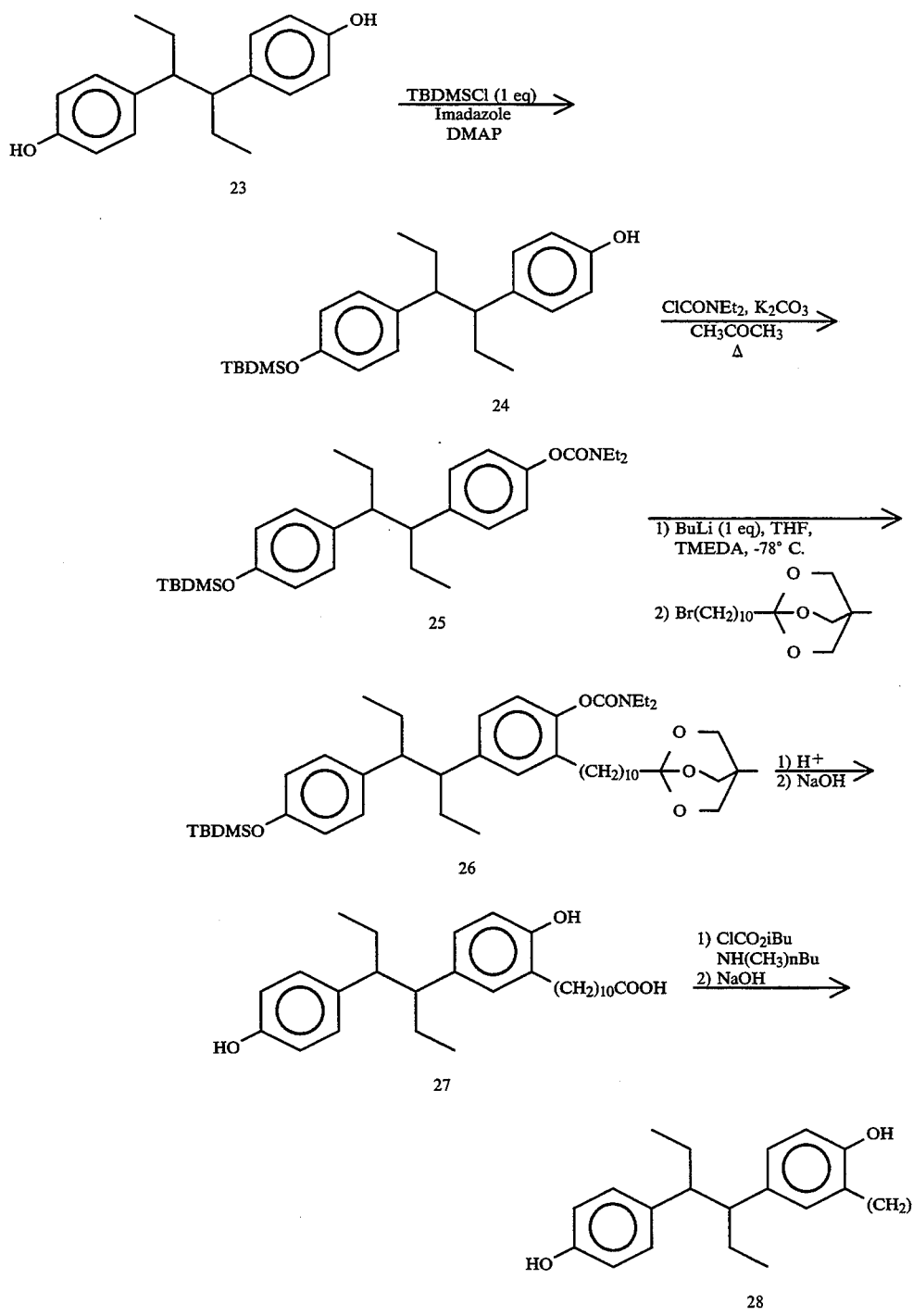
Synthesis G -continued N-butyl, N-methyl-[6'-hydroxy-2'-(4-hydroxyphenyl)-(1', 2'-dihydronaphtalen-3'-yl) undecanoic amide (34)

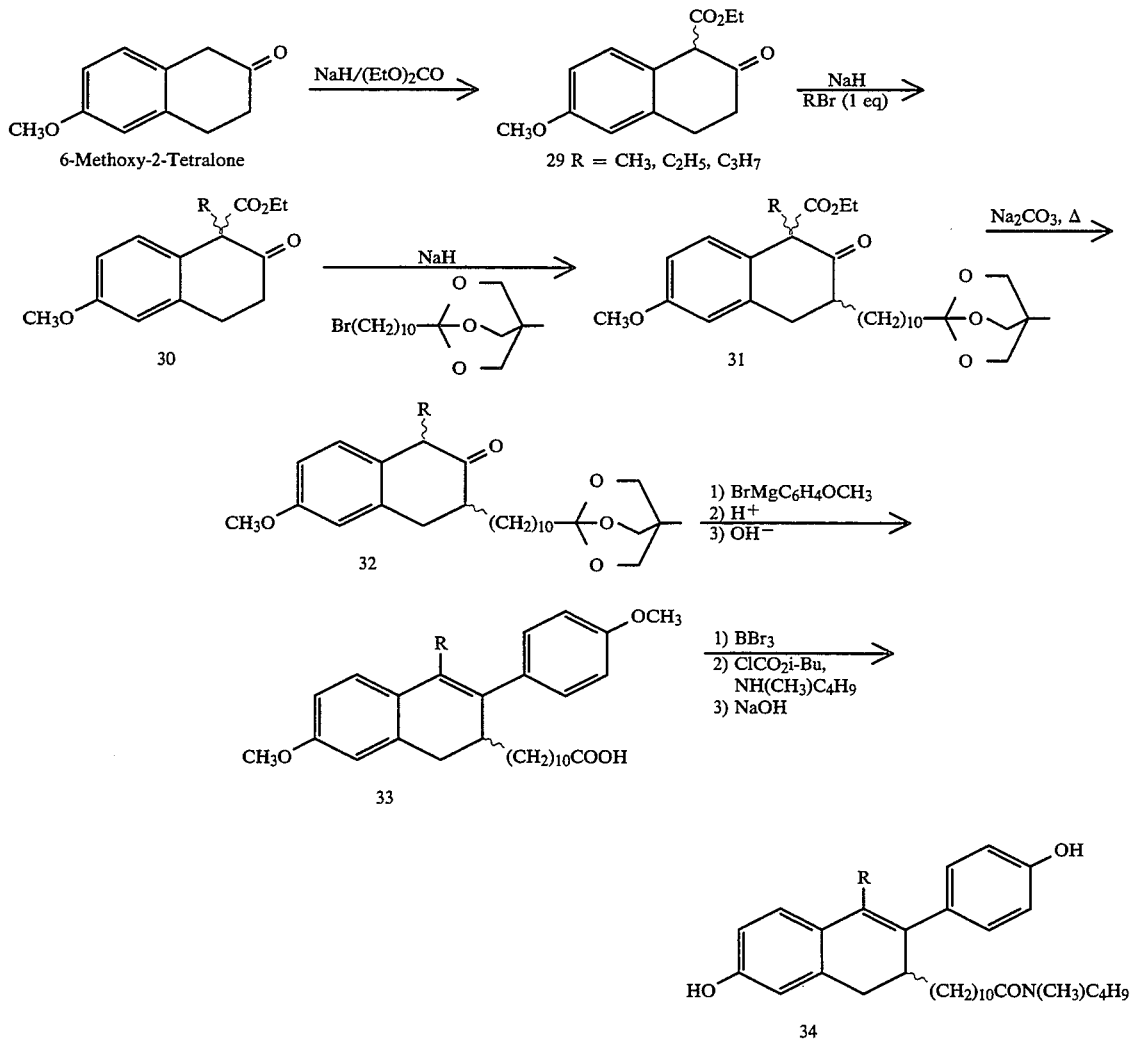

The terms and descriptions used herein are preferred embodiments set forth by way of illustration only, and are not intended as limitations on the many variations which those of skill in the art will recognize to be possible in practicing the present invention as defined by the following claims.

What is claimed is:

1. A pharmaceutical composition comprising a pharmaceutically acceptable diluent or carrier and a therapeutically effective amount of an antiestrogen of the formula:

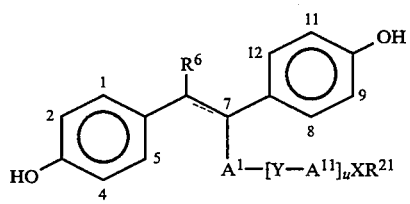

wherein $R^6$ is methyl or ethyl; where the dotted line represents an optional double bond of configuration;
wherein $A^1$ and $A^{11}$ are the same or different and are either absent or selected from the group consisting of straight-chain alkylene and branched-chain alkylene, $A^1$ and $A^{11}$ together having a total of from 3 to 20 carbon atoms;
wherein Y is phenylene;
wherein $R_{21}$ is selected from the group consisting of hydrogen, straight or branched-chain lower alkyl, lower alkenyl, and lower alkynyl,
wherein X is $CONR_{23}$, $R_{23}$ being hydrogen or lower alkyl;
and wherein $\mu$ is an integer from 0 to 5.

2. A pharmaceutical composition comprising a pharmaceutically acceptable diluent or carrier and a therapeutically effective amount of an antiestrogen having the molecular formula:

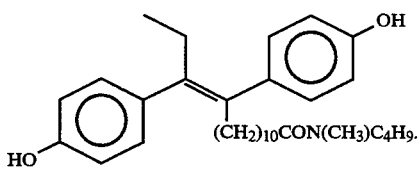

3. An antiestrogenic compound having the molecular formula:

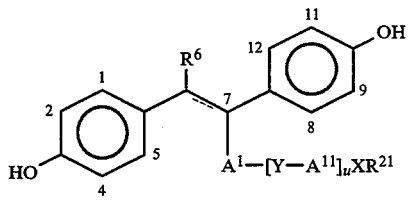

wherein $R^6$ is methyl or ethyl; where the dotted line represents an optional double bond of configuration;

wherein $A^1$ and $A^{11}$ are the same or different and are either absent or selected from the group consisting of a straight- or branched-chain alkylene, $A^1$ and $A^{11}$ together having a total of from 3 to 20 carbon atoms;

wherein Y is phenylene;

wherein $R_{21}$ is selected from the group consisting of hydrogen, straight or branched-chain lower alkyl, lower alkenyl, and lower alkynyl wherein X is $-CONR_{23}-$, $R_{23}$ being hydrogen or lower alkyl;

and wherein $\mu$ is an integer from 0 to 5.

4. An antiestrogenic compound having the molecular formula:

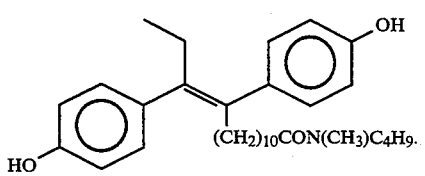

* * * * *